(12) United States Patent
Shigeta

(10) Patent No.: US 10,743,772 B2
(45) Date of Patent: Aug. 18, 2020

(54) PHOTOACOUSTIC IMAGING APPARATUS

(71) Applicant: CYBERDYNE Inc., Tsukuba-shi, Ibaraki (JP)

(72) Inventor: Yusuke Shigeta, Tokyo (JP)

(73) Assignee: CYBERDYNE Inc., Tsukuba-shi (JP)

( * ) Notice: Subject to any disclaimer, the term of this patent is extended or adjusted under 35 U.S.C. 154(b) by 310 days.

(21) Appl. No.: 15/755,994

(22) PCT Filed: Aug. 31, 2016

(86) PCT No.: PCT/JP2016/075583
§ 371 (c)(1),
(2) Date: Feb. 27, 2018

(87) PCT Pub. No.: WO2017/038907
PCT Pub. Date: Mar. 9, 2017

(65) Prior Publication Data
US 2018/0263500 A1 Sep. 20, 2018

(30) Foreign Application Priority Data
Aug. 31, 2015 (JP) .................. 2015-171335

(51) Int. Cl.
*A61B 5/095* (2006.01)
*A61B 5/00* (2006.01)
(Continued)

(52) U.S. Cl.
CPC .......... *A61B 5/0095* (2013.01); *A61B 8/4444* (2013.01); *G01N 29/226* (2013.01);
(Continued)

(58) Field of Classification Search
CPC ................ A61B 5/0095; A61B 5/4444; G01N 2291/02475; G01N 29/226; G01N 29/2418; G01N 29/28
See application file for complete search history.

(56) References Cited

U.S. PATENT DOCUMENTS

| | | | |
|---|---|---|---|
| 2014/0345385 | A1 | 11/2014 | Irisawa et al. |
| 2015/0168354 | A1 | 6/2015 | Kandori |
| 2015/0173626 | A1 | 6/2015 | Irisawa et al. |

FOREIGN PATENT DOCUMENTS

| | | | |
|---|---|---|---|
| JP | 2013-188330 A | 9/2013 |
| JP | 2013-188465 A | 9/2013 |

(Continued)

OTHER PUBLICATIONS

International Search Report (PCT/ISA/210) issued in PCT Application No. PCT/JP2016/075583 dated Oct. 4, 2016 with English translation (four pages).
(Continued)

*Primary Examiner* — Mark D Ramaly
(74) *Attorney, Agent, or Firm* — Crowell & Moring LLP

(57) ABSTRACT

This optoacoustic imaging device is provided with: a light source part for irradiating an object to be inspected with light; an ultrasonic vibrator for detecting an acoustic wave generated from a subject to be detected in the object to be inspected which has absorbed the light emitted from the light source part; and a detecting part disposed in a probe body and including an acoustic lens disposed closer to the tip side of the probe body than the ultrasonic vibrator, wherein the acoustic lens is configured to have a light absorbance of 1-30% and a light reflectance of less than 85% with respect to light which has a wavelength band of 650-1000 nm and is emitted from the light source part.

8 Claims, 12 Drawing Sheets

(51) Int. Cl.
  *G01N 29/22* (2006.01)
  *A61B 8/00* (2006.01)
  *G01N 29/24* (2006.01)
  *G01N 29/28* (2006.01)

(52) U.S. Cl.
  CPC ......... *G01N 29/2418* (2013.01); *G01N 29/28* (2013.01); *G01N 2291/02475* (2013.01)

(56) References Cited

FOREIGN PATENT DOCUMENTS

| | | |
|---|---|---|
| JP | 2014-68751 A | 4/2014 |
| JP | 2015-112326 A | 6/2015 |

OTHER PUBLICATIONS

Japanese-language Written Opinion (PCT/ISA/237) issued in PCT Application No. PCT/JP2016/075583 dated Oct. 4, 2016 (three pages).

ACOUSTIC WAVE GENERATION TEST

PHOTOACOUSTIC IMAGING APPARATUS

TECHNICAL FIELD

The present invention relates to a photoacoustic imaging apparatus, particularly, to a photoacoustic imaging apparatus including an acoustic lens.

BACKGROUND ART

A photoacoustic imaging apparatus including an acoustic lens has conventionally been known (see patent literature 1, for example).

Patent literature 1 discloses a photoacoustic imaging apparatus including a Q switch solid-state laser source (light source portion) that emits light to a test object. The photoacoustic imaging apparatus includes a detecting portion arranged at a probe body. The detecting portion includes an inorganic transducer (ultrasonic transducer) that detects an acoustic wave generated from a detection target in the test object when the detection target absorbs light emitted from the Q switch solid-state laser source, and an acoustic lens arranged closer to the tip of the probe body than the inorganic transducer.

CITATION LIST

Patent Literatures

Patent Literature 1: Japanese Patent Laying-Open No. 2013-188330

SUMMARY OF INVENTION

Technical Problem

In the above-described photoacoustic imaging apparatus described in patent literature 1, if light emitted from the Q switch solid-state laser source and reflected from the test object is absorbed in large quantities by the acoustic lens, the acoustic lens expands thermally. In this case, an acoustic wave may be generated from the acoustic lens. If light emitted from the Q switch solid-state laser source and reflected from the test object is not absorbed much by the acoustic lens, the light is transmitted through the acoustic lens and reaches the inorganic transducer (ultrasonic transducer) to be absorbed by the inorganic transducer. In this case, an acoustic wave may be generated from the inorganic transducer. These cases cause a problem of the occurrence of artifact resulting from an acoustic wave generated from the acoustic lens or the inorganic transducer (ultrasonic transducer) when an image is formed based on an acoustic wave.

The present invention has been made to solve the above-described problem. It is one object of the present invention to provide a photoacoustic imaging apparatus capable of reducing the occurrence of artifact resulting from an acoustic wave generated from an acoustic lens or an ultrasonic transducer when an image is formed based on an acoustic wave.

Solution to Problem

A photoacoustic imaging apparatus according to one aspect of the present invention comprises: a light source portion that emits light to a test object; and a detecting portion arranged at a probe body. The detecting portion comprises an ultrasonic transducer and an acoustic lens. The ultrasonic transducer detects an acoustic wave generated from a detection target in the test object when the detection target absorbs light emitted from the light source portion. The acoustic lens is arranged closer to a tip of the probe body than the ultrasonic transducer. The acoustic lens is configured to have a light absorption ratio from 1 to 30% and a light reflectance of less than 85% in a wavelength region from 650 to 1000 nm of light emitted from the light source portion.

As described above, the acoustic lens provided in the photoacoustic imaging apparatus according to the one aspect of the present invention is configured to have a light absorption ratio from 1 to 30% and a light reflectance of less than 85% in a wavelength region from 650 to 1000 nm of light emitted from the light source portion. By properly adjusting the light absorption ratio in a range from 1 to 30% while adjusting the light reflectance to a value of less than 85% in this way, absorption of large quantities of light emitted from the light source portion and reflected from the test object (excessive absorption) by the acoustic lens can be suppressed. This makes it possible to suppress generation of an acoustic wave from the acoustic lens due to thermal expansion of the acoustic lens. Further, properly adjusting the light absorption ratio in a range from 1 to 30% while adjusting the light reflectance to a value of less than 85% makes it possible to suppress unintentional transmission of much of light emitted from the light source portion and reflected from the test object through the acoustic lens. This makes it possible to suppress generation of an acoustic wave from the ultrasonic transducer due to absorption of the light having been transmitted through the acoustic lens by the ultrasonic transducer. As a result, the occurrence of artifact resulting from an acoustic wave generated from the acoustic lens or the ultrasonic transducer can be reduced.

In the photoacoustic imaging apparatus according to the one aspect of the present invention, the acoustic lens is preferably configured to have a light transmittance of 20% or less in a wavelength region from 650 to 1000 nm of light emitted from the light source portion. With this configuration, the light transmittance is adjusted to a value of 20% or less in addition to the light reflectance of the acoustic lens, thereby allowing the acoustic lens to have a proper light absorption ratio easily. As a result, the occurrence of artifact resulting from an acoustic wave generated from the acoustic lens or the ultrasonic transducer can be reduced more easily when an image is formed based on an acoustic wave.

In the photoacoustic imaging apparatus according to the one aspect of the present invention, the light source portion is preferably configured to emit light with a maximum output of 300 kW or less. By setting the maximum output from the light source portion at 300 kW or less in this way, absorption of large quantities of light emitted from the light source portion and reflected from the test object (excessive absorption) by the acoustic lens can be suppressed easily.

In the photoacoustic imaging apparatus according to the one aspect of the present invention, the acoustic lens is preferably configured to have a light absorption ratio of greater than 10% and not exceeding 20% in a wavelength region from 730 to 935 nm of light emitted from the light source portion. Setting the light absorption ratio of the acoustic lens in a range from a value of greater than 10% to a value not exceeding 20% in this way makes it possible to suppress absorption of large quantities of light emitted from the light source portion and reflected from the test object (suppress excessive absorption) by the acoustic lens more effectively. Further, unintentional transmission of much of light emitted from the light source portion and reflected from the test object through the acoustic lens can be suppressed more effectively.

In the photoacoustic imaging apparatus according to the one aspect of the present invention, the acoustic lens is preferably configured to have a thickness from 0.5 to 2 mm. By setting the thickness of the acoustic lens in a range from 0.5 to 2 mm in this way, the acoustic lens can be formed to have a moderate volume. This allows suppression of thermal expansion of the acoustic lens while achieving a compact configuration of the detecting portion.

In the photoacoustic imaging apparatus according to the one aspect of the present invention, the light source portion is preferably formed using an LED element. This configuration allows reduction in power consumption of the light source portion, size reduction of the apparatus, and reduction in the occurrence of artifact resulting from an acoustic wave generated from the acoustic lens or the ultrasonic transducer when an image is formed based on an acoustic wave, compared to a configuration where the light source portion is formed using a solid-state laser source.

In the photoacoustic imaging apparatus according to the one aspect of the present invention, the light source portion is preferably formed using a semiconductor laser element. This configuration allows reduction in power consumption of the light source portion and size reduction of the apparatus, compared to a configuration where the light source portion is formed using a solid-state laser source. Further, a laser beam of relatively high directivity can be emitted to the test object, so that much of light from the semiconductor laser element can be emitted to the test object. Additionally, the occurrence of artifact resulting from an acoustic wave generated from the acoustic lens or the ultrasonic transducer can be reduced.

In the photoacoustic imaging apparatus according to the one aspect of the present invention, the light source portion is preferably formed using an organic semiconductor element. This configuration allows reduction in power consumption of the light source portion and size reduction of the apparatus, compared to a configuration where the light source portion is formed using a solid-state laser source. Further, using an organic light-emitting diode element capable of being reduced easily in thickness facilitates size reduction of the light source portion where the light-emitting element is provided. Additionally, the occurrence of artifact resulting from an acoustic wave generated from the acoustic lens or the ultrasonic transducer can be reduced.

Advantageous Effects of Invention

As described above, according to the present invention, the occurrence of artifact resulting from an acoustic wave generated from the acoustic lens or the ultrasonic transducer can be reduced.

DESCRIPTION OF EMBODIMENT

An embodiment of the present invention will be described below based on the drawings.

(Overall Configuration of Photoacoustic Imaging Apparatus)

The overall configuration of a photoacoustic imaging apparatus 100 according to the embodiment of the present invention will be described by referring to FIGS. 1 to 12. The photoacoustic imaging apparatus 100 has the function of detecting an acoustic wave A from a detection target Q (blood, organ, or puncture needle, for example) inside a test object P (human body, for example), and forming an image based on a detection signal.

Figure 1:
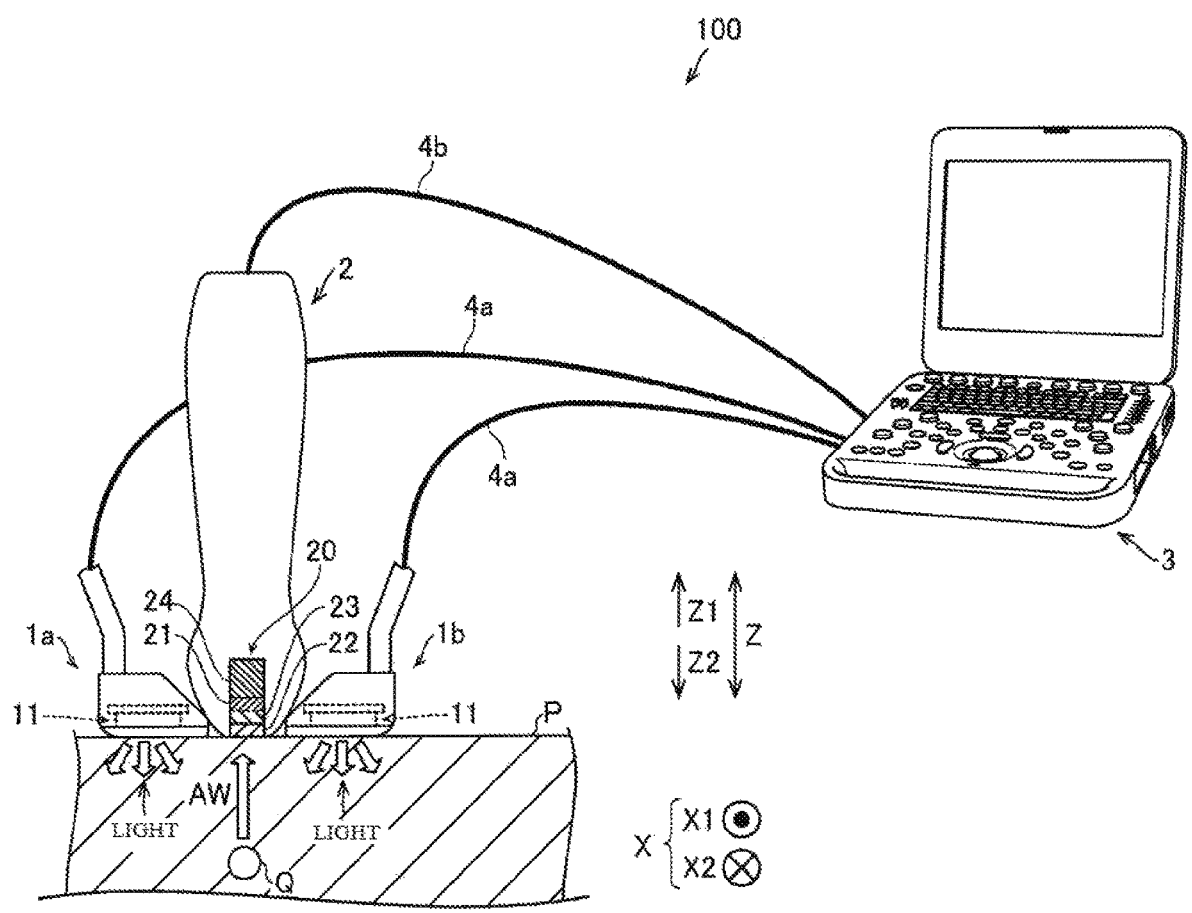
FIG. 1 is a schematic view showing the overall configuration of a photoacoustic imaging apparatus according to an embodiment of the present invention.

As shown in FIG. 1, the photoacoustic imaging apparatus 100 according to the embodiment of the present invention includes an illumination portion 1a and an illumination portion 1b, a probe body 2, and an apparatus body 3. The photoacoustic imaging apparatus 100 includes a cable 4a for connecting the illumination portion 1a (1b) and the apparatus body 3, and a cable 4b for connecting the probe body 2 and the apparatus body 3.

(Configuration of Illumination Portion (Light Source Portion))

The illumination portions 1a and 1b are provided as a pair. The illumination portions 1a and 1b are arranged adjacent to the probe body 2. The illumination portions 1a and 1b are arranged so as to sandwich the probe body 2. The illumination portions 1a and 1b are placed on a surface of the test object P when a test is conducted by using the photoacoustic imaging apparatus 100. The illumination portions 1a and 1b each include a light source portion 11.

The light source portion 11 is configured to emit light (pulsed light) toward the test object P. Various light sources are applicable to the light source portion 11. The light source portion 11 is formed using an LED element (light-emitting diode element), for example. The light source portion 11 is configured to be capable of emitting light with a maximum output of 300 kW or less, for example. A maximum output of light emitted from the light source portion 11 is determined as follows: (average output)/(pulse width)×(repetition frequency). The light source portion 11 is configured to emit light having a predetermined wavelength responsive to the type of the LED element. For example, the light source portion 11 is configured to emit light of 650 nm, 750 nm, 850 nm, or 940 nm, which is determined in response to the type of the LED element.

The light source portion 11 includes a plurality of LED elements connected in series. The light source portion 11 (illumination portion 1a or 1b) is configured to be capable of emitting light having such an intensity as to allow formation of an image of the detection target Q in the test object P to the test object P. The light source portion 11 is configured to be capable of emitting pulsed light having a wavelength (a wavelength of about 850 nm, for example) in an infrared region at which the pulsed light is caused to enter a human body comparatively easily (than visible light) by receiving drive power supplied from a light source drive circuit 32 in the apparatus body 3.

(Configuration of Probe Body)

The probe body 2 is configured as a linear ultrasonic probe, for example. A tip portion (a portion closer to a Z2 side) of the probe body 2 is placed on the surface of the test object P when a test is conducted by using the photoacoustic imaging apparatus 100. The probe body 2 includes a detecting portion 20.

The detecting portion 20 includes an ultrasonic transducer 21, an acoustic lens 22, an acoustic matching layer 23, and a backing material 24. The acoustic lens 22, the acoustic matching layer 23, the ultrasonic transducer 21, and the backing material 24 are arranged by being connected (stacked) on each other in this order as viewed from the tip (Z2 side) of the probe body 2. The acoustic lens 22 is arranged closer to the tip of the probe body 2 than the ultrasonic transducer 21.

The ultrasonic transducer 21 includes a plurality of ultrasonic transducers 21 (the ultrasonic transducer 21 is configured to have a plurality of channels). For example, the number of these channels is 128. The ultrasonic transducers 21 are spaced from each other at predetermined intervals in an X direction and are arranged in an array pattern. The ultrasonic transducer 21 is configured to be capable of emitting an ultrasonic wave B1 to the test object P in response to application of a voltage (drive voltage). The ultrasonic transducer 21 is further configured to be caused to vibrate by the acoustic wave A and an ultrasonic wave B2 from the detection target Q in the test object P, and transmit the vibration as a voltage (detection signal) to the apparatus body 3. In this way, the ultrasonic transducer 21 becomes capable of detecting the acoustic wave A generated from the detection target Q in the test object P when the detection target Q absorbs light emitted from the light source portion 11. Specifically, the ultrasonic transducer 21 is configured to be capable of transmitting and receiving ultrasonic waves.

An ultrasonic wave referred to in this description means a sound wave (elastic wave) having such a high frequency as not to cause a sensation of hearing of a person with normal hearing ability and is a concept of a sound wave of about 16000 Hz or more. In this description, light emitted from the light source portion 11 is absorbed by the detection target Q in the test object P to generate an ultrasonic wave and this ultrasonic wave will be called an "acoustic wave (acoustic wave A)." An ultrasonic wave generated from the detecting portion 20 described later and reflected on the detection target Q in the test object P will simply be called an "ultrasonic wave."

The acoustic lens 22 is configured to focus the ultrasonic wave B1 into the test object P when the ultrasonic wave B1 is emitted from the ultrasonic transducer 21 to the test object P. The acoustic lens 22 is configured to focus the acoustic wave A or the ultrasonic wave B2 on the ultrasonic transducer 21 when the acoustic wave A or the ultrasonic wave B2 from the test object P enters the acoustic lens 22. The acoustic lens 22 will be described in detail later.

The acoustic matching layer 23 has an acoustic impedance between the acoustic impedance of the ultrasonic transducer 21 and that of the test object P (or substantially the same as the acoustic impedance of the ultrasonic transducer 21 or that of the test object P). The acoustic matching layer 23 is configured to match the acoustic impedance of the ultrasonic transducer 21 and that of the test object P. The acoustic matching layer 23 may have one layer or multiple layers.

The backing material 24 is arranged behind the ultrasonic transducer 21 (on a Z1 side). The backing material 24 is configured to suppress backward propagations of the ultrasonic waves B1 and B2.

(Configuration of Apparatus Body)

The apparatus body 3 is configured to control emission of light from the light source portion 11 (illumination portion 1a or 1b), and control drive of the ultrasonic transducer 21 of the detecting portion 20. The apparatus body 3 includes a display portion 31. The apparatus body 3 is configured to form an image of a signal from detection signals (acoustic wave A and ultrasonic wave B2) acquired from the detecting portion 20, and display the resultant image on the display portion 31.

Figure 2:
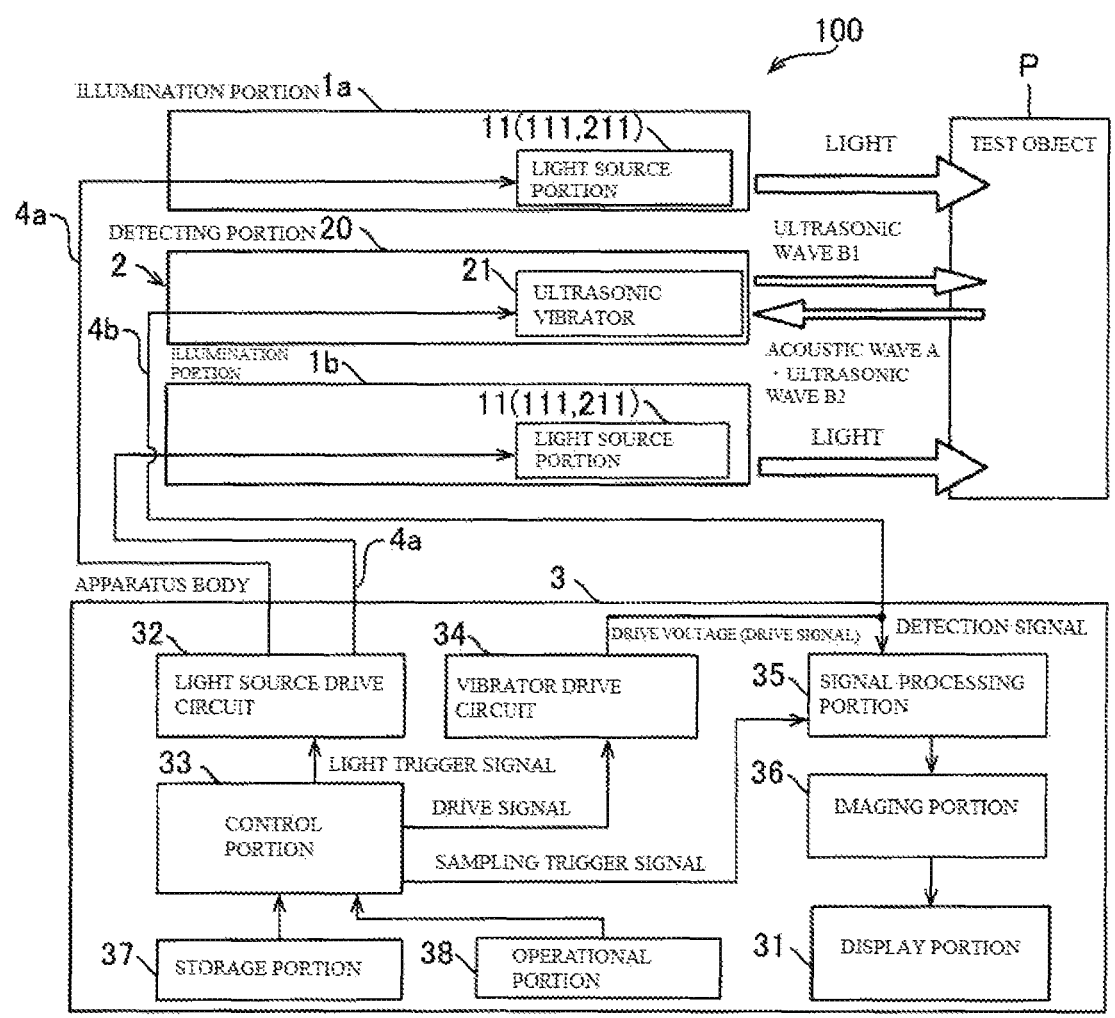
FIG. 2 is a block diagram showing the overall configuration of the photoacoustic imaging apparatus according to the embodiment of the present invention.

As shown in FIG. 2, the apparatus body 3 includes the display portion 31, the light source drive circuit 32, a control portion 33, a transducer drive circuit 34, a signal processing portion 35, an imaging portion 36, a storage portion 37, and an operational portion 38.

The light source drive circuit 32 is configured to acquire power from an external power supply or a battery (not shown in the drawings), for example. The light source drive circuit 32 is configured to supply the power to the light source portion 11 based on a light trigger signal from the control portion 33. For example, the light source drive circuit 32 is capable of making the light source portion 11 emit pulsed light having a repetition frequency of 1 kHz and a pulse width (full width at half maximum) of about 100 ns (or about 150 ns) to the test object P in response to a light trigger signal having a repetition frequency of 1 kHz.

The control portion 33 is configured to control the photoacoustic imaging apparatus 100 entirely. For example, the control portion 33 controls drive of the ultrasonic transducer 21 by transmitting a drive signal to the transducer drive circuit 34. Further, the control portion 33 controls drive of the light source portion 11 through the light source drive circuit 32 by transmitting a light trigger signal to the light source drive circuit 32. The control portion 33 also controls signal processing on a detection signal by transmitting a sampling trigger signal synchronized with the light trigger signal to the signal processing portion 35.

The transducer drive circuit 34 is configured to apply a drive voltage responsive to the drive signal to each of the channels of the ultrasonic transducers 21. In this way, the transducer drive circuit 34 is configured to drive the respective channels of the ultrasonic transducers 21 independently in response to the drive signal from the control portion 33.

The signal processing portion 35 is configured to acquire a detection signal from the detecting portion 20 (ultrasonic transducer 21) in response to the sampling trigger signal. The signal processing portion 35 is configured to transmit the acquired signal to the imaging portion 36.

The imaging portion 36 is configured to acquire the detection signal transmitted from the signal processing portion 35, perform processing such as reconstruction on the detection signal, and form a photoacoustic wave image. The display portion 31 is formed using a liquid crystal panel, for example, and is configured to display the photoacoustic wave image formed by the imaging portion 36.

The storage portion 37 is configured to be capable of storing a given type of information.

The operational portion 38 is configured to accept input operation by an operator and is configured to transmit information given by the accepted input operation to the control portion 33.

(Configuration of Acoustic Lens)

The configuration of the acoustic lens 22 will be described in detail below.

The acoustic lens 22 is mainly made of silicone rubber. Specifically, the base material of the acoustic lens 22 is silicone rubber. The acoustic lens 22 contains an inorganic substance of a predetermined amount. More specifically, the acoustic lens 22 contains a substance other than silicone rubber (an inorganic substance made of metal (hereinafter simply called an "inorganic substance") and a nonmetallic substance) in such a manner that the substance other than silicone rubber constitutes 43 wt % of the total mass of the acoustic lens 22. The inorganic substance in the acoustic lens 22 is Na (sodium), Al (aluminum), Ca (calcium), Fe (iron), Sn (tin), and Ce (cerium), for example. In addition to these metals, the acoustic lens 22 contains multiple types of metallic elements of tiny and undetectable amounts. The inclusion of such inorganic substances makes the acoustic lens 22 have an opalescent color.

The acoustic lens 22 is configured to have a thickness from 0.5 to 2 mm (a thickness of about 1.5 mm, for example) in a direction (Z direction) in which the probe body 2 extends.

In this embodiment, the acoustic lens 22 is configured to have a predetermined light absorption ratio Pa in a measurement wavelength region (a light wavelength region used for formation of an image). The light absorption ratio Pa is determined by the following formula (1):

$$Pa = Po - Pr - Pt \ldots \quad \text{formula (1),}$$

where Po is the total energy of light (total light quantity) emitted to the acoustic lens 22 set at 100%:

Pr is a light reflectance at the acoustic lens; and
Pt is a light transmittance at the acoustic lens 22.

Figure 3:
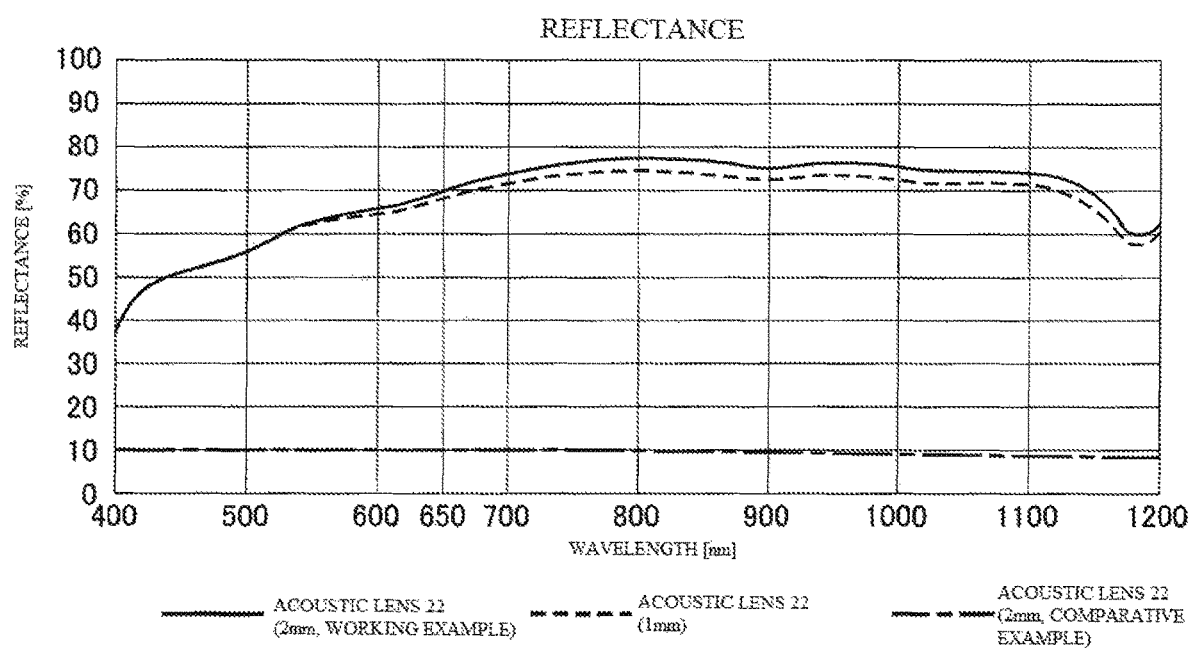
FIG. 3 is a view showing the reflectance of an acoustic lens in the photoacoustic imaging apparatus according to the embodiment of the present invention.

FIG. 3 shows the reflectance of the acoustic lens 22 and the reflectance of an acoustic lens of a comparative example 1. A solid line shows the reflectance of the acoustic lens 22 of this embodiment having a thickness of 2 mm. A dotted line shows the reflectance of the acoustic lens 22 of this embodiment having a thickness of 1 mm. Alternate long and short dashed lines show the reflectance of a black acoustic lens (comparative example 1) different from the acoustic lens 22 of this embodiment.

As shown in FIG. 3, the acoustic lens 22 is configured to have a light reflectance of less than 85% in a measurement wavelength region (a light wavelength region used for formation of an image). Preferably, the acoustic lens 22 is configured to have a light reflectance of less than 85% in a wavelength region from 650 to 1000 nm of light emitted from the light source portion 11. More preferably, the acoustic lens 22 is configured to have a light reflectance of less than 80% in a light wavelength region from 650 to 1000 nm.

Figure 4:
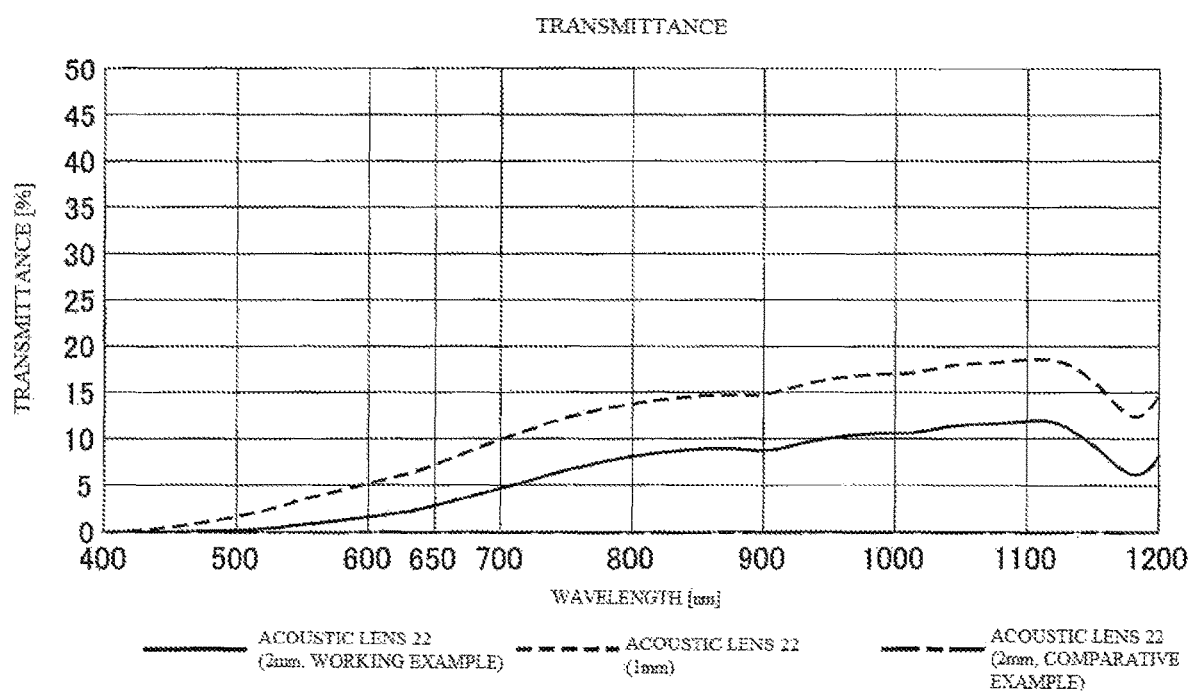
FIG. 4 is a view showing the transmittance of the acoustic lens in the photoacoustic imaging apparatus according to the embodiment of the present invention.

FIG. 4 shows the transmittance of the acoustic lens 22 and the transmittance of the acoustic lens of the comparative example 1. A solid line shows the transmittance of the acoustic lens 22 of this embodiment having a thickness of 2 mm. A dotted line shows the transmittance of the acoustic lens 22 of this embodiment having a thickness of 1 mm. Alternate long and short dashed lines show the transmittance of the black acoustic lens (comparative example 1) different from the acoustic lens 22 of this embodiment.

As shown in FIG. 4, the acoustic lens 22 is configured to have a light transmittance of 20% or less in a measurement wavelength region. Preferably, the acoustic lens 22 is configured to have a light transmittance of 20% or less in a wavelength region from 650 to 1000 nm of light emitted from the light source portion 11.

Figure 5:
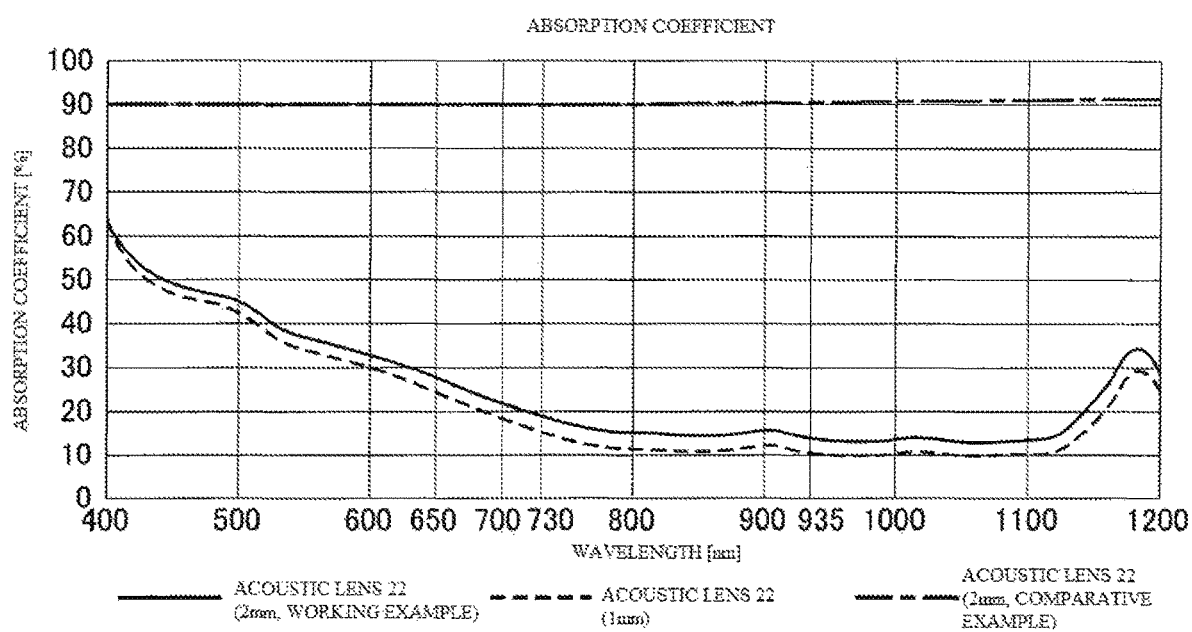
FIG. 5 is a view showing the absorption ratio of the acoustic lens in the photoacoustic imaging apparatus according to the embodiment of the present invention.

FIG. 5 shows Pa (absorption ratio), which is a value obtained by subtracting Pt (reflectance) shown in FIG. 3 and Pt (transmittance) shown in FIG. 4 from Po (total energy (100%) of light emitted to the acoustic lens 22) based on the formula (1).

FIG. 5 shows the transmittance of the acoustic lens 22 and the absorption ratio of the acoustic lens of the comparative example 1. A solid line shows the absorption ratio of the acoustic lens 22 of this embodiment having a thickness of 2 mm. A dotted line shows the absorption ratio of the acoustic lens 22 of this embodiment having a thickness of 1 mm. Alternate long and short dashed lines show the absorption ratio of the black acoustic lens (comparative example 1) different from the acoustic lens 22 of this embodiment.

As shown in FIG. 5, in this embodiment, the acoustic lens 22 has an absorption ratio from 1 to 30% in a measurement wavelength region. Preferably, the acoustic lens 22 is configured to have a light absorption ratio from 1 to 30% in a wavelength region from 650 to 1000 nm of light emitted from the light source portion 11.

As described above, setting the light absorption ratio of the acoustic lens 22 at 30% or less in a wavelength region from 650 to 1000 nm makes it possible to suppress absorption of large quantities of light emitted from the light source portion 11 and reflected from the test object P (suppress excessive absorption) by the acoustic lens 22. This makes it possible to suppress generation of the acoustic wave A from the acoustic lens 22 due to thermal expansion of the acoustic lens 22. Further, setting the light absorption ratio of the acoustic lens 22 at 1% or more makes it possible to suppress unintentional transmission of much of light emitted from the light source portion 11 and reflected from the test object P through the acoustic lens. This makes it possible to suppress generation of the acoustic wave A from the ultrasonic transducer 21 due to absorption of the light having been transmitted through the acoustic lens 22 by the ultrasonic transducer 21.

More preferably, the acoustic lens 22 is configured to have a light absorption ratio of greater than 10% and not exceeding 20% in a wavelength region from 730 to 935 nm of light emitted from the light source portion 11. The acoustic lens 22 exhibits a light absorption ratio of 10.1% in response to emission of light having a wavelength of 935 nm. This shows that the light absorption ratio of the acoustic lens 22 tends to increase with reduction in the wavelength of light to be emitted from 935 nm.

As described above, setting the light absorption ratio of the acoustic lens 22 at 20% or less in a wavelength region from 650 to 1000 nm makes it possible to suppress absorption of large quantities of light emitted from the light source portion 11 and reflected from the test object P (suppress excessive absorption) by the acoustic lens 22 more than setting the light absorption ratio of the acoustic lens 22 to be greater than 20% and not to exceed 30%. Further, setting the light absorption ratio of the acoustic lens 22 to be greater than 10% makes it possible to suppress unintentional transmission of much of light emitted from the light source portion 11 and reflected from the test object P through the acoustic lens more than setting the light absorption ratio of the acoustic lens 22 to range from 1 to 10%.

Working Example

The following describes an acoustic wave generation test conducted by using an acoustic lens to confirm the effect of the present invention. More specifically, as a working example corresponding to the above-described embodiment, the acoustic wave generation test was conducted by using the following acoustic lens of the working example. Further, as comparative examples, the acoustic wave generation test was conducted by using the following acoustic lens of the comparative example 1 and the following acoustic lens of a comparative example 2.

Working Example

Figure 6:
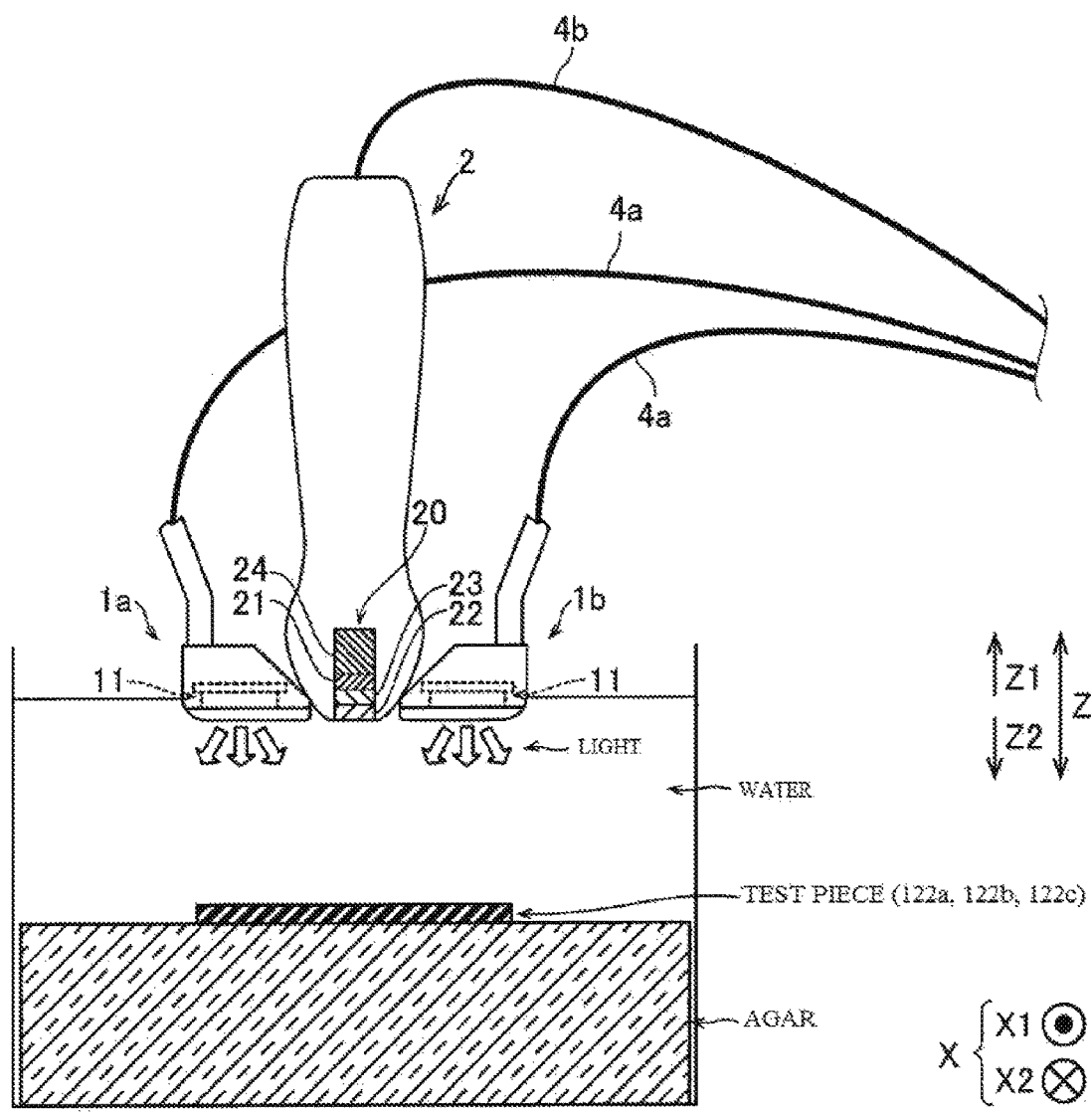
FIG. 6 is a view for explaining a device used for conducting an acoustic wave generation test using an acoustic lens.

The acoustic lens 22 was formed to a thickness of 2 mm and placed at a predetermined position under water shown in FIG. 6. The acoustic lens 22 has the optical characteristics shown in FIGS. 3 to 5 (working example).

For the sake of convenience, the acoustic lens 22 of the working example placed at the predetermined position under water shown in FIG. 6 will be called a test piece 122*a*.

Comparative Example 1

The acoustic lens used in the comparative example 1 was formed to a thickness of 2 mm. The acoustic lens of the comparative example 1 was placed at the predetermined position under water shown in FIG. 6. The acoustic lens of the comparative example 1 is mainly made of silicone rubber and contains an inorganic substance different from that of the working example. Thus, unlike the acoustic lens 22 of the working example, the acoustic lens of the comparative example 1 has a black color. The acoustic lens of the comparative example 1 has the optical characteristics shown in FIGS. 3 to 5 (comparative example 1). For the sake of convenience, the acoustic lens of the comparative example 1 placed at the predetermined position under water shown in FIG. 6 will be called a test piece 122*b*.

Comparative Example 2

The acoustic lens used in the comparative example 2 was formed by coating (sputtering) of the outer surface of the acoustic lens 22 of the working example having a thickness of 2 mm with aluminum. The applied aluminum has a thickness of 20 μm. The acoustic lens of the comparative example 2 was placed at the predetermined position under water shown in FIG. 6. For the sake of convenience, the acoustic lens of the comparative example 2 placed at the predetermined position under water shown in FIG. 6 will be called a test piece 122*c*.

(Acoustic Wave Generation Test)

The acoustic wave generation test was conducted as follows. More specifically, as shown in FIG. 6, agar was sunk to the bottom of a water tank filled with water and the acoustic lenses (test pieces 122*a* to 122*c*) were placed on the upper surface of the agar. Then, the illumination portion 1*a* (1*b*) and the probe body 2 were arranged so as to dip the tip portions of the illumination portion 1*a* (1*b*) and the probe body 2 in water near a water surface and to make these tip portions face the test pieces 122*a* to 122*c* under water. The agar was prepared to adjust the height positions of the test pieces 122*a* to 122*c* under water to be subjected to the acoustic wave generation test. In this state, light of 850 nm was emitted with an output of 1 kW from the illumination portion 1*a* (1*b*) toward the acoustic lens, and an image was formed based on the acoustic wave A detected by the detecting portion 20 (ultrasonic transducer 21). Images shown in FIGS. 7 to 9 were obtained while the test pieces 122*a* to 122*c* were arranged at a distance (depth) of about 2 cm from the detecting portion 20 of the probe body 2.

Figure 7:
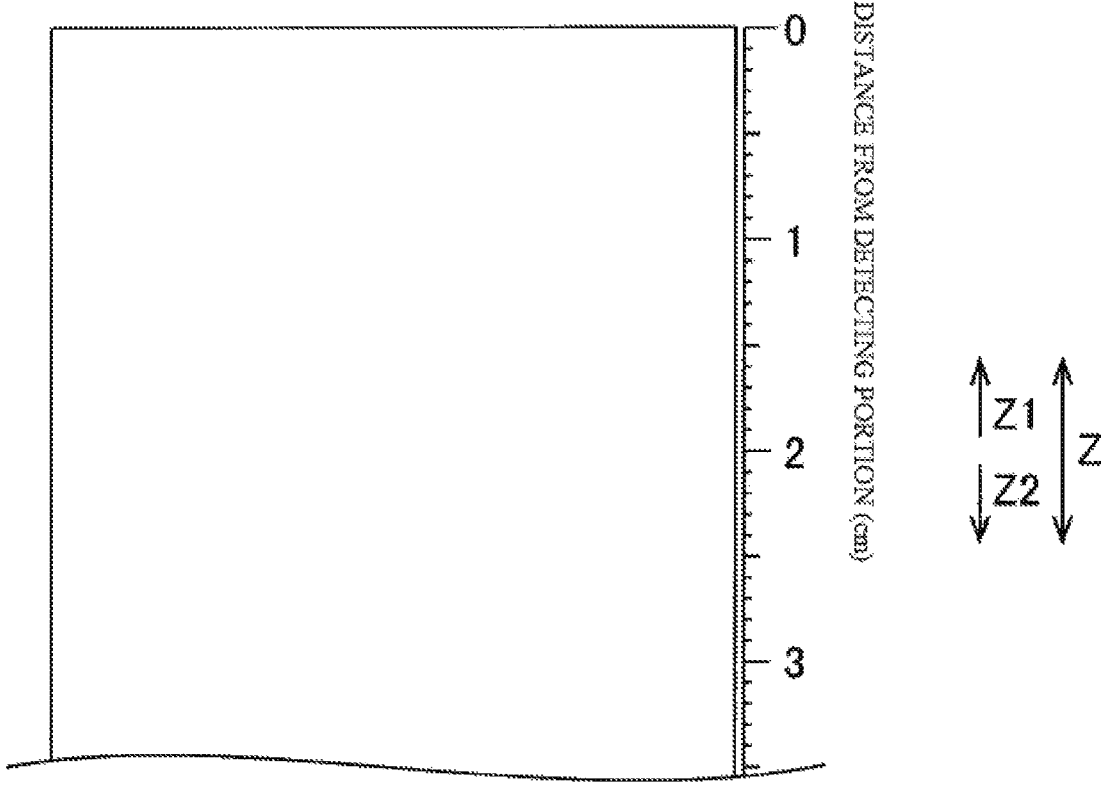
FIG. 7 is a view for explaining the acoustic wave generation test conducted by using an acoustic lens according to a working example.
Figure 8:
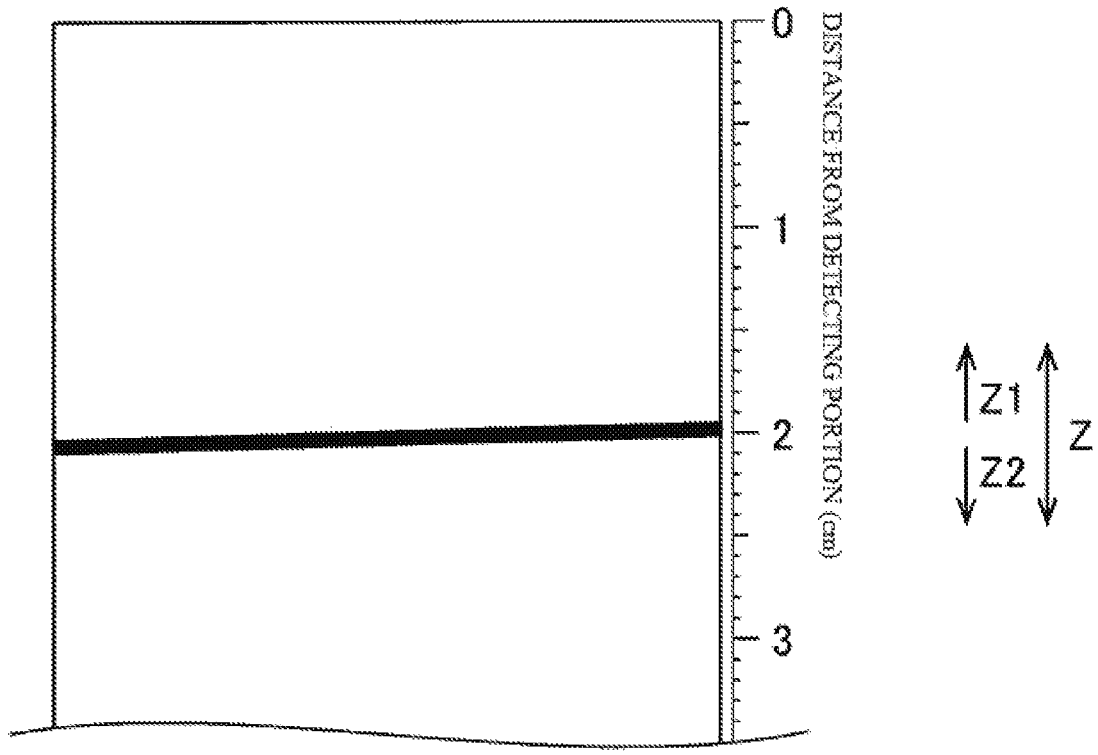
FIG. 8 is a view for explaining the acoustic wave generation test conducted by using an acoustic lens according to a comparative example 1.
Figure 9:
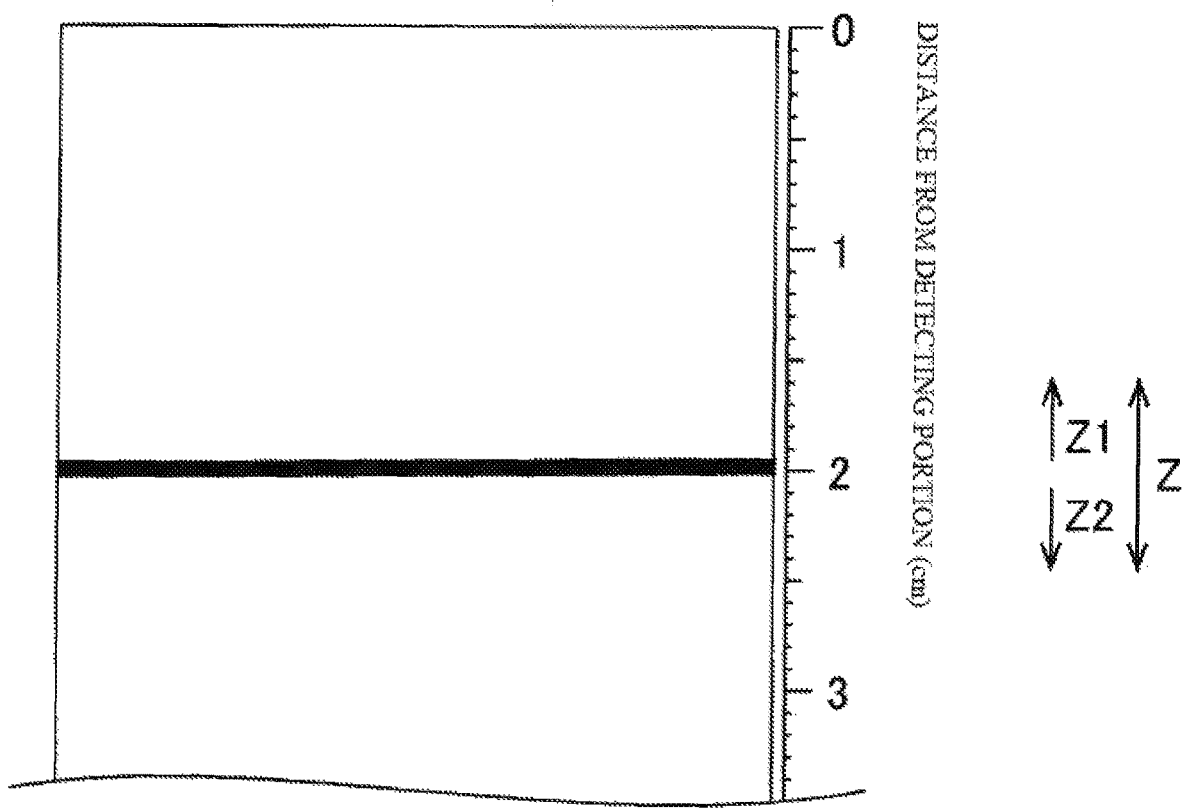
FIG. 9 is a view for explaining the acoustic wave generation test conducted by using an acoustic lens according to a comparative example 2.

FIGS. 7 to 9 show results of the acoustic wave generation test on the test pieces 122*a* to 122*c* respectively. In each of FIGS. 7 to 12, a scale on the right side shows a distance (depth) from the detecting portion 20.

As shown in FIG. 7, as a result of the acoustic wave generation test conducted by emitting light to the test piece 122*a* (the acoustic lens 22 of the working example placed under water), an image resulting from an acoustic wave generated by absorption of the light by the test piece 122*a* was not confirmed. Specifically, this shows that substantially no acoustic wave A was generated from the test piece 122*a* having received the light.

As shown in FIG. 8, as a result of the acoustic wave generation test conducted by emitting light to the test piece 122*b* (the acoustic lens of the comparative example 1 placed under water), an image resulting from the acoustic wave A generated by absorption of the light by the test piece 122*b* was confirmed. Specifically, this shows that the acoustic wave A was generated from the test piece 122*b* having received the light.

As shown in FIG. 9, as a result of the acoustic wave generation test conducted by emitting light to the test piece 122*c* (the acoustic lens of the comparative example 2 placed under water (acoustic lens formed by coating the outer surface of the acoustic lens 22 with aluminum)), an image resulting from the acoustic wave A was confirmed. This acoustic wave A is considered to be generated by absorption of the light by the aluminum and resultant thermal expansion of the acoustic lens. This shows that generation of an acoustic wave cannot be suppressed by coating the surface of the acoustic lens 22 with aluminum (metal).

(Relationship Between Light Output and Resultant Acoustic Wave)

Figure 10:
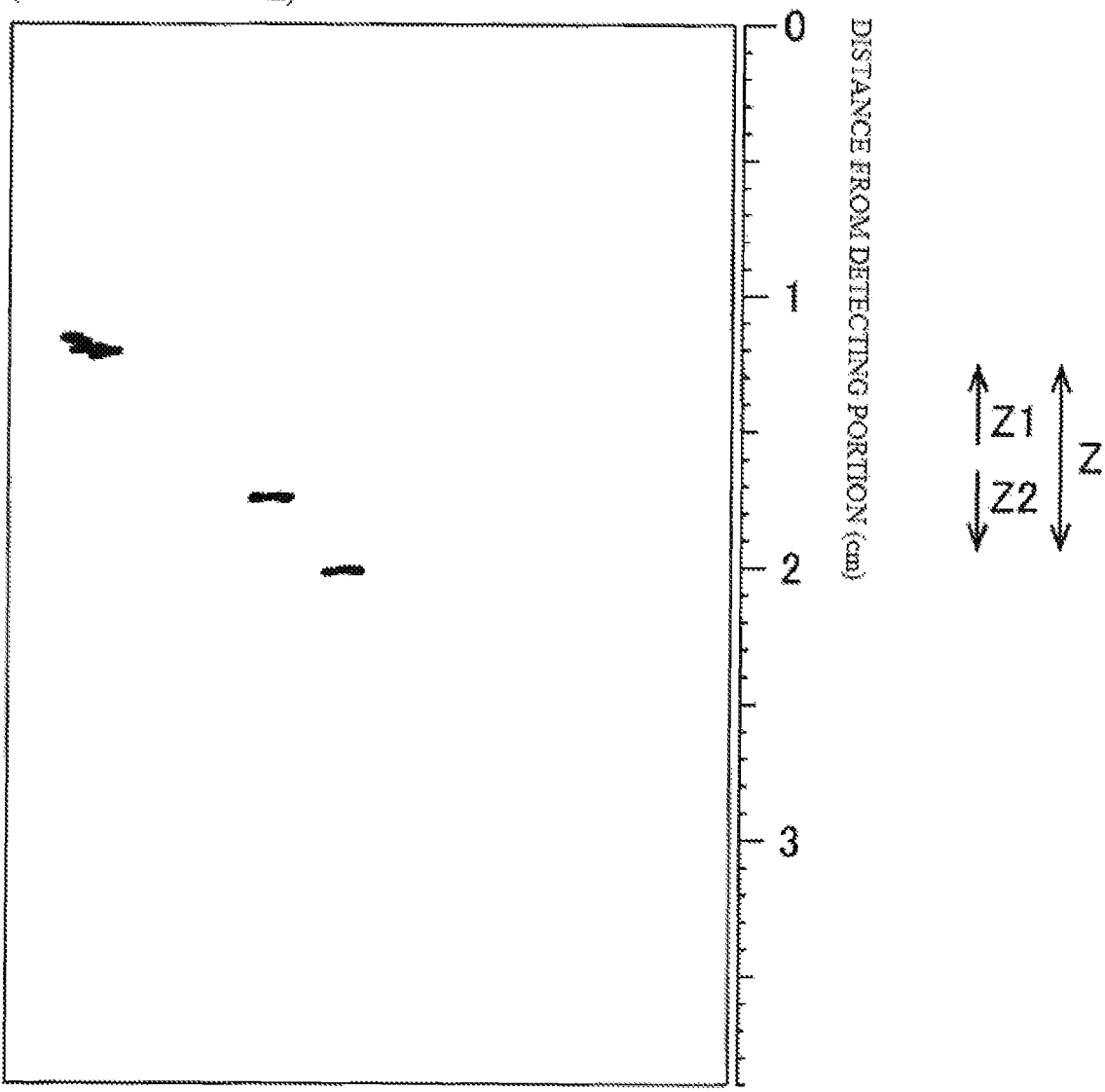
FIG. 10 is a view for explaining the acoustic wave generation test conducted by emitting light with an output of 333 kW to the acoustic lens according to the working example.
Figure 11:
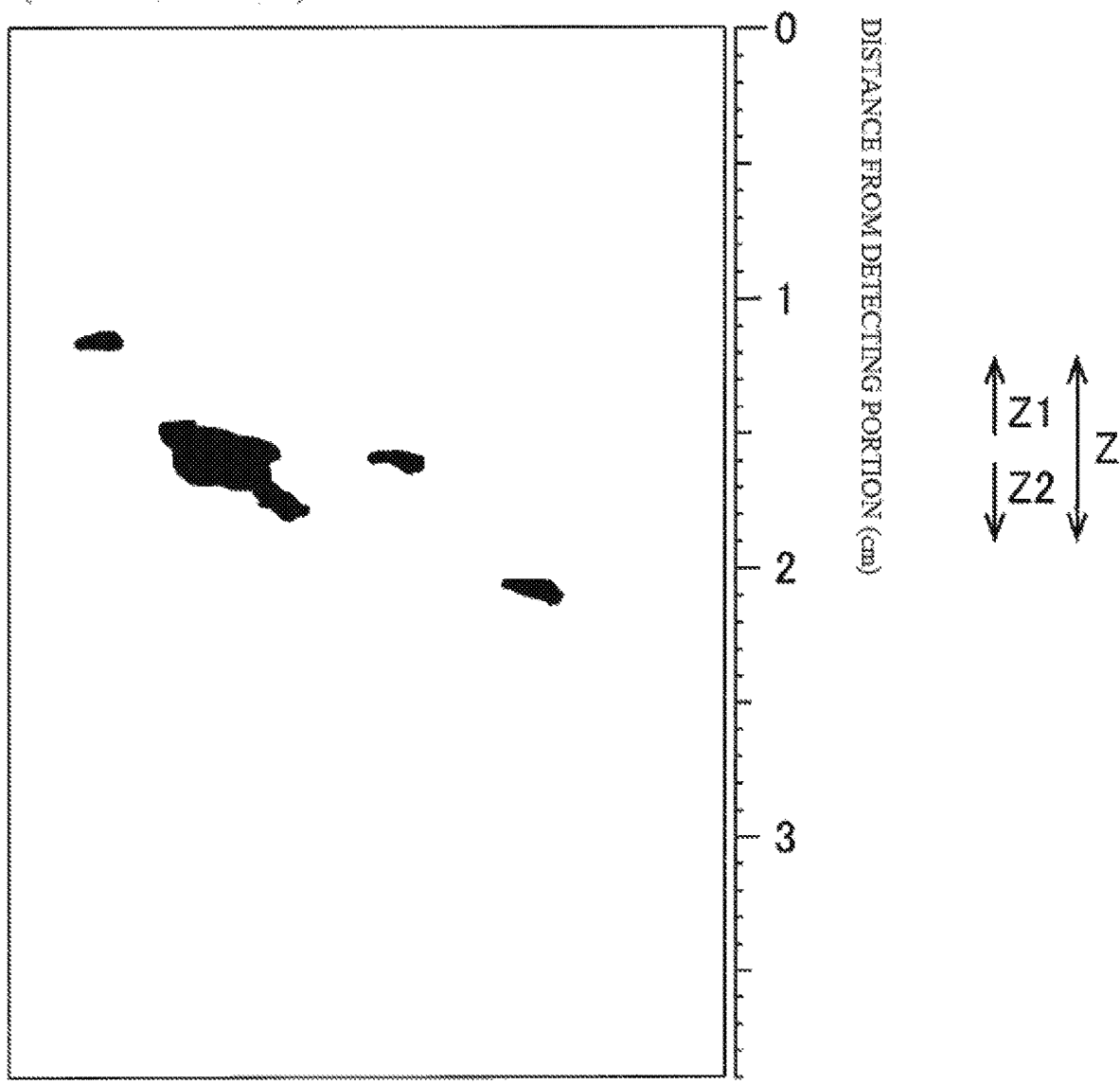
FIG. 11 is a view for explaining the acoustic wave generation test conducted by emitting light with an output of 1 MW to the acoustic lens according to the working example.
Figure 12:
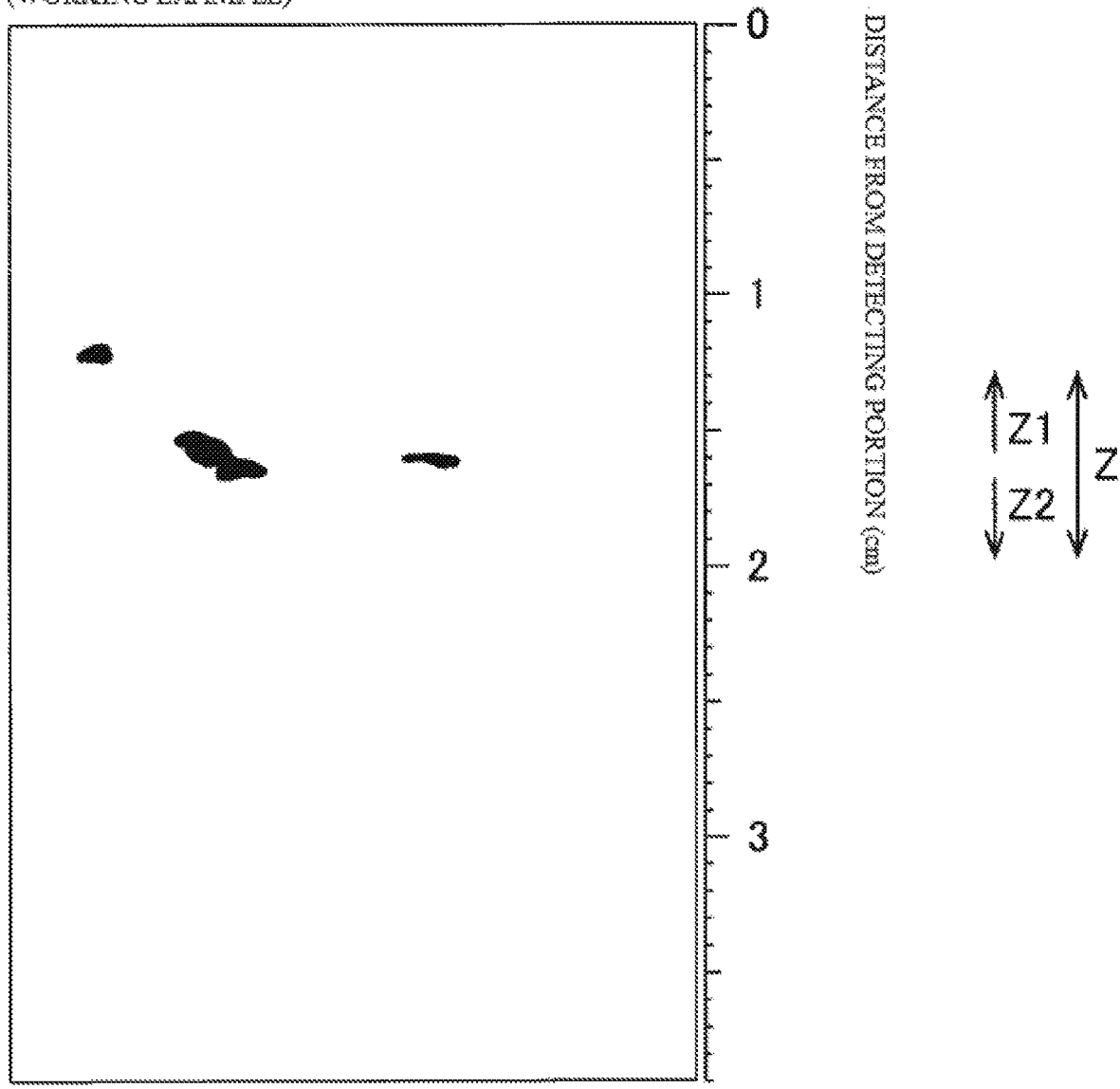
FIG. 12 is a view for explaining the acoustic wave generation test conducted by emitting light with an output of 500 kW to the acoustic lens according to the working example.

Next, a test was conducted to examine a relationship between light output and the resultant acoustic wave A. More specifically, by following the same test method described by referring to FIG. 6, light with an output of 333 kW, light with an output of 1 MW, and light with an output of 500 kW were emitted from the illumination portion 1*a* (1*b*) toward the test piece 122*a* (the acoustic lens 22 of the working example placed under water), and images were formed based on the acoustic wave A detected by the detecting portion 20 (ultrasonic transducer 21). FIGS. 10 to 12 each show a result of the test conducted to examine a relationship between a corresponding output of the light emitted to the test piece 122*a* and the resultant acoustic wave A. The images shown in FIGS. 10 to 12 were obtained while the test piece 122a was placed at a distance (depth) of about 1.5 cm from the detecting portion 20 of the probe body 2.

FIG. 10 shows an image formed based on the acoustic wave A detected by the detecting portion 20 (ultrasonic transducer 21) in response to emission of light with a maximum output of 333 kW (with an average output of 40 mW, a pulse width of 6 ns, and a repetition frequency of 20 Hz) to the test piece 122a (the acoustic lens 22 under water). In response to emission of the light with a maximum output of 333 kW to the test piece 122a, a tiny image (pattern) resulting from the acoustic wave A generated by absorption of the light by the test piece 122a was confirmed. However, this image (pattern) of such a level has substantially no distinction from noise in an image on the display portion 31 (see FIG. 2). This shows that, even if artifact resulting from the acoustic wave A generated from the test piece 122a is caused in response to emission of the light with an output of 333 kW to the test piece 122a, the generated acoustic wave A is only at a level that causes no problem in forming an actual image of the detection target Q.

FIG. 11 shows an image formed based on the acoustic wave A detected by the detecting portion 20 (ultrasonic transducer 21) in response to emission of light with a maximum output of 1 MW (with an average output of 120 mW, a pulse width of 6 ns, and a repetition frequency of 20 Hz) to the test piece 122a (the acoustic lens 22 under water). An image resulting from the acoustic wave A generated by absorption of the light by the test piece 122a was confirmed in response to emission of the light with a maximum output of 1 MW to the test piece 122a.

FIG. 12 shows an image formed based on the acoustic wave A detected by the detecting portion 20 (ultrasonic transducer 21) in response to emission of light with a maximum output of 500 kW (with an average output of 60 mW, a pulse width of 6 ns, and a repetition frequency of 20 Hz) to the test piece 122a (the acoustic lens 22 under water). An image resulting from the acoustic wave A generated by absorption of the light by the test piece 122a was confirmed in response to emission of the light with a maximum output of 500 kW to the test piece 122a.

The test result in FIG. 11 (maximum output of 1 MW) and the test result in FIG. 12 (maximum output of 500 kW) show that the acoustic wave A to cause adverse effect in formation of an image is generated from the test piece 122a (acoustic lens 22) having received light of at least 500 kW or more.

The test result in FIG. 10 shows that substantially no acoustic wave A is generated (the acoustic wave A to cause adverse effect in formation of an image is not generated) from the test piece 122a (acoustic lens 22) having received light of 333 kW. This shows that, in terms of reducing generation of the acoustic wave A resulting from absorption of light by the test piece 122a (acoustic lens 22), a maximum output of light to be used for operating the photoacoustic imaging apparatus 100 is preferably 300 kW or less.

Effect of this Embodiment

This embodiment is capable of achieving the following effects.

As described above, the acoustic lens 22 provided in this embodiment is configured to have a light absorption ratio from 1 to 30% and a light reflectance of less than 85% in a wavelength region from 650 to 1000 nm of light emitted from the light source portion 11. By properly adjusting the light absorption ratio in a range from 1 to 30% while adjusting the light reflectance to a value of less than 85% in this way, absorption of large quantities of light emitted from the light source portion 11 and reflected from the test object P (excessive absorption) by the acoustic lens 22 can be suppressed. This makes it possible to suppress generation of the acoustic wave A from the acoustic lens 22 due to thermal expansion of the acoustic lens 22. Further, properly adjusting the light absorption ratio in a range from 1 to 30% while adjusting the light reflectance to a value of less than 85% makes it possible to suppress unintentional transmission of much of light emitted from the light source portion 11 and reflected from the test object P through the acoustic lens 22. This makes it possible to suppress generation of the acoustic wave A from the ultrasonic transducer 21 due to absorption of the light having been transmitted through the acoustic lens 22 by the ultrasonic transducer 21. As a result, the occurrence of artifact resulting from the acoustic wave A generated from the acoustic lens 22 or the ultrasonic transducer 21 can be reduced.

The acoustic lens 22 provided in this embodiment is configured to have a light transmittance of 20% or less in a wavelength region from 650 to 1000 nm of light emitted from the light source portion 11. By adjusting the light transmittance to a value of 20% or less in this way in addition to the light reflectance of the acoustic lens 22, the acoustic lens 22 is allowed to have a proper light absorption ratio easily. As a result, the occurrence of artifact resulting from the acoustic wave A generated from the acoustic lens 22 or the ultrasonic transducer 21 can be reduced more easily when an image is formed based on the acoustic wave A.

The light source portion 11 provided in this embodiment is configured to emit light with a maximum output of 300 kW or less. By setting the maximum output from the light source portion at 300 kW or less in this way, absorption of large quantities of light emitted from the light source portion 11 and reflected from the test object P (excessive absorption) by the acoustic lens 22 can be suppressed easily.

The acoustic lens 22 provided in this embodiment is configured to have a light absorption ratio of greater than 10% and not exceeding 20% in a wavelength region from 730 to 935 nm of light emitted from the light source portion 11. Setting the light absorption ratio of the acoustic lens 22 in a range from a value of greater than 10% to a value not exceeding 20% in this way makes it possible to suppress absorption of large quantities of light emitted from the light source portion 11 and reflected from the test object P (suppress excessive absorption) by the acoustic lens 22 more effectively. Further, unintentional transmission of much of light emitted from the light source portion 11 and reflected from the test object P through the acoustic lens 22 can be suppressed more effectively.

The acoustic lens 22 provided in this embodiment is configured to have a thickness from 0.5 to 2 mm. By setting the thickness of the acoustic lens 22 in a range from 0.5 to 2 mm in this way, the acoustic lens 22 can be formed to have a moderate volume. This allows suppression of thermal expansion of the acoustic lens 22 while achieving a compact configuration of the detecting portion 20.

In this embodiment, the light source portion 11 is formed using an LED element. This allows reduction in power consumption of the light source portion 11, size reduction of the apparatus, and reduction in the occurrence of artifact resulting from the acoustic wave A generated from the acoustic lens 22 or the ultrasonic transducer 21 when an image is formed based on the acoustic wave A, compared to a configuration where the light source portion 11 is formed using a solid-state laser source.

[Modifications]

The embodiment and the working example disclosed herein must be considered to be illustrative in all aspects and not restrictive. The range of the present invention is understood not by the above descriptions of the embodiment and the working example but by the scope of claims for patent. All changes (modifications) within the meaning and range equivalent to the scope of claims for patent are to be embraced.

For example, the acoustic lens provided in the example described in the embodiment and the working example above has a light absorption ratio of greater than 10% and not exceeding 20% in a wavelength region from 730 to 935 nm of light emitted from the light source portion. However, this is not to limit the present invention. An acoustic lens applicable to the present invention may have different optical characteristics, as long as this acoustic lens is configured to have a light absorption ratio from 1 to 30% and a light reflectance of less than 85% in a wavelength region from 650 to 1000 nm of light emitted from the light source portion.

The acoustic lens in the example of the above-described embodiment and working example has a light transmittance of 20% or less in a wavelength region from 650 to 1000 nm of light emitted from the light source portion. However, this is not to limit the present invention. An acoustic lens applicable to the present invention may have a light transmittance of greater than 20% in a wavelength region from 650 to 1000 nm of light emitted from the light source portion, as long as this acoustic lens is configured to have a light absorption ratio from 1 to 30% and a light reflectance of less than 85% in a wavelength region from 650 to 1000 nm of light emitted from the light source portion.

The acoustic lens in the example of the above-described embodiment has a thickness from 0.5 to 2 mm and the acoustic lens in the example of the above-described working example has a thickness of 2 mm. However, this is not to limit the present invention. In the present invention, the acoustic lens may alternatively be configured to have a thickness of greater than 2 mm. Still alternatively, the acoustic lens may be configured to have a thickness of less than 0.5 mm.

In the example of the above-described embodiment and in the example of the above-described working example, the light source portion is formed using an LED element. However, this is not to limit the present invention. In the present invention, a semiconductor laser element 111 (see FIG. 2) or an organic semiconductor element 211 (see FIG. 2) is applicable for forming the light source portion, for example.

REFERENCE SIGNS LIST

2 Probe body
11 LED element (light source portion)
20 Detecting portion
21 Ultrasonic transducer
100 Photoacoustic imaging apparatus
111 Semiconductor laser element (light source portion)
211 Organic semiconductor element (light source portion)
P Test object
Q Detection target

The invention claimed is:

1. A photoacoustic imaging apparatus comprising:
a light source portion that emits light to a test object; and
a detecting portion arranged at a probe body, the detecting portion comprising an ultrasonic transducer and an acoustic lens, the ultrasonic transducer detecting an acoustic wave generated from a detection target in the test object when the detection target absorbs light emitted from the light source portion, the acoustic lens being arranged closer to a tip of the probe body than the ultrasonic transducer, wherein
the acoustic lens is configured to have a light absorption ratio from 1 to 30% and a light reflectance of less than 85% in a wavelength region from 650 to 1000 nm of light emitted from the light source portion.

2. The photoacoustic imaging apparatus according to claim 1, wherein the acoustic lens is configured to have a light transmittance of 20% or less in a wavelength region from 650 to 1000 nm of light emitted from the light source portion.

3. The photoacoustic imaging apparatus according to claim 1, wherein the light source portion is configured to emit light with a maximum output of 300 kW or less.

4. The photoacoustic imaging apparatus according to claim 1, wherein the acoustic lens is configured to have a light absorption ratio of greater than 10% and not exceeding 20% in a wavelength region from 730 to 935 nm of light emitted from the light source portion.

5. The photoacoustic imaging apparatus according to claim 1, wherein the acoustic lens is configured to have a thickness from 0.5 to 2 mm.

6. The photoacoustic imaging apparatus according to claim 1, wherein the light source portion is formed using an LED element.

7. The photoacoustic imaging apparatus according to claim 1, wherein the light source portion is formed using a semiconductor laser element.

8. The photoacoustic imaging apparatus according to claim 1, wherein the light source portion is formed using an organic semiconductor element.

* * * * *